United States Patent [19]

Boegesoe et al.

[11] Patent Number: 4,946,863

[45] Date of Patent: Aug. 7, 1990

[54] CNS-AFFECTING 6-OXY-3-AMINOMETHYL INDANES, COMPOSITIONS THEREOF, AND METHOD OF TREATING THEREWITH

[75] Inventors: Klaus P. Boegesoe, Lyngby; Jens K. Perregaard, Oelstykke, both of Denmark

[73] Assignee: H. Lundbeck A/S, Copenhagen-Valby, Denmark

[21] Appl. No.: 298,630

[22] Filed: Jan. 18, 1989

Related U.S. Application Data

[62] Division of Ser. No. 155,354, Feb. 12, 1988, Pat. No. 4,847,254.

[30] Foreign Application Priority Data

Feb. 26, 1987 [GB] United Kingdom ............... 8704572

[51] Int. Cl.$^5$ ................. A61K 31/13; C07C 87/06
[52] U.S. Cl. .................. 514/447; 514/480; 514/512; 514/529; 514/532; 514/540; 514/546; 514/655; 549/68; 558/271; 558/272; 558/273; 560/24; 560/27; 560/32; 560/108; 560/115; 560/116; 560/134; 560/139; 564/387
[58] Field of Search .............. 564/387, 306, 336; 560/24, 133, 107, 138, 27, 32, 108, 116, 139; 558/260, 270, 275, 277, 271, 272, 273; 514/512, 529, 532, 544, 546, 655, 657, 549, 649, 447, 480, 540; 549/68

[56] References Cited

U.S. PATENT DOCUMENTS

| | | | |
|---|---|---|---|
| 3,419,560 | 12/1968 | Bernstein et al. | 564/306 |
| 3,886,168 | 5/1975 | Himmele et al. | 546/205 |
| 4,057,573 | 11/1977 | Haas et al. | 560/139 |
| 4,505,932 | 3/1985 | DeBernardis et al. | 564/387 |

FOREIGN PATENT DOCUMENTS 53-05146 1/1978 Japan .

OTHER PUBLICATIONS

Gaino et al., Chem. Abs., vol. 88, No. 23, entry #169822x (1978).
Lahiri et al., J. Pharm. Sci., vol. 57 (6), pp. 1013–1016 (1968)
DeBernardis et al., J. Med. Chem., vol. 28 (10), pp. 1398–1404 (1985).
Bogeso et al., J. Med. Chem., vol. 30, pp. 142–150 (1987).
Nichols et al., Chem. Abs., vol. 99, No. 23, entry #194583e (1983).

*Primary Examiner*—Anton H. Sutto
*Assistant Examiner*—Andrew G. Rozycki
*Attorney, Agent, or Firm*—Gordon W. Hueschen

[57] ABSTRACT

The present invention relates to 3-aminomethyl derivatives of indane, dihydrobenzofurane, dihydrobenzothiophene, and indoline, acid addition salts thereof, isomers thereof, methods of preparation, pharmaceutical compositions and method of treating CNS-disorders such as schizophrenia, Parkinson's disease, depression, anxiety, migraine and senile dementia, or in the cure of cardiovascular diseases, by administering such a derivative.

11 Claims, No Drawings

CNS-AFFECTING 6-OXY-3-AMINOMETHYL INDANES, COMPOSITIONS THEREOF, AND METHOD OF TREATING THEREWITH

This is a division of application Ser. No. 155,354, filed Feb. 12, 1988, now U.S. Pat. No. 4,847,254 issued 7-11-89.

BACKGROUND OF THE INVENTION

Damping of dopamine (DA) overactivity is an important principle in the treatment of various CNS-disorders such as schizophrenia and dyskinesia. This can be acheived by using postsynaptic DA-receptor blockers (neuroleptics) the use of which, however, is accompanied by several side-effects.

An alternative principle in order to inhibit DA function is to stimulate presynaptic DA-receptors (DA-autoreceptors) which inhibit DA-cell firing. This principle has been used with some success administering low doses of apomorphine to patients with schizophrenia and tardive dyskinesias. However, apomorphine has no selective action at DA autoreceptors since postsynaptic DA receptors are stimulated by slightly higher doses than those necessary for presynaptic DA receptors, leading to excitation.

Stimulation of central DA-receptors is also a well established treatment of Parkinson's disease.

SUMMARY OF THE INVENTION

However, according to the present invention it has now surprisingly been found that indane-, dihydrobenzofurane-, dihydrobenzothiophene-, and indoline- derivatives of the following formula:

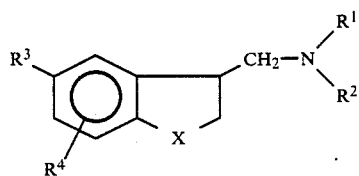

I wherein

X is $CH_2$, $R^1$ is hydrogen, lower alkyl (1–6 C-atoms) or lower alkenyl (1–6 C-atoms), branched or unbranched, optionally substituted with a hydroxy group, aralkyl with from 4–13 C-atoms inclusive, the aromatic group being phenyl, thienyl, imidazolyl, pyridyl or pyrimidyl, or cycloalkyl (3–6 C-atoms), $R^2$ is hydrogen, lower alkyl (1–6 C-atoms), branched or unbranched, provided that both $R^1$ and $R^2$ may not be hydrogen, $R^3$ is hydroxy, optionally substituted with

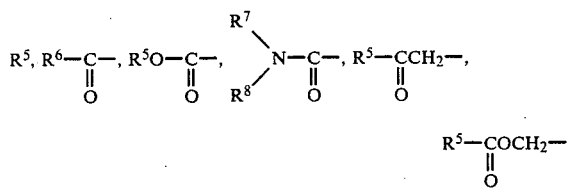

in which $R^5$ is alkyl (1–20 C-atoms), branched or unbranched, cycloalkyl (3–6 C-atoms), adamantyl, aralkyl (4–13 C-atoms inclusive) or an optionally substituted phenyl group, $R^6$ is hydrogen or as $R^5$, $R^7$ and $R^8$ are defined as $R^6$, $R^4$ is hydrogen, halogen, lower alkyl (1–6 C-atoms), branched or unbranched, trifluoromethyl, cyano, nitro, SH, or $NH_2$ optionally substituted as shown above for $R^3$, as well as isomers thereof, or a pharmaceutically acceptable acid addition salt thereof, are effective at presynaptic DA receptors, or both at pre- and postsynaptic DA-receptors, indicating usefulness in the treatment of disorders of the central nervous system (CNS) such as schizophrenia or Parkinson's disease.

The 1-aminomethyl derivatives of Formula I exist as optical isomers, and the useful effects are often found in the single enantiomers to a different degree.

All the aforesaid enantiomers fall within the scope of the present invention. Also the methods of isolation of such enantiomers, wellknown to the art, fall within the scope of the present invention.

Some of the 1-aminomethylindanes of Formula I have been broadly disclosed in U.S. Pat. No. 3,886,168. However, compounds explicitly described in this patent as e.g. our compound Lu 21-091 (see Table I) are without any DA stimulating properties. 4,5-Dihydroxy substituted indanes of the above type I are adrenergic agents which are claimed to be beneficial in the treatment of hypertension. Included in e.g. U.S. Pat. No. 4,505,932.

As examples of lower alkyl or lower alkenyl groups may be mentioned methyl, ethyl, n-propyl, isopropyl, n-butyl, isobutyl, n-amyl, n-hexyl, allyl, 2-propenyl, or the like.

As examples of aralkyl groups may be mentioned benzyl, phenethyl, 2-thienylethyl, 3-thienylethyl, 1-imidazolylethyl, 2-thiazolylethyl or the like.

In the compounds of Formula I, X is preferably $CH_2$, O, or S, $R^3$ is hydroxy or an acylated derivative thereof. $R^4$ is hydrogen. $R^1$ and $R^2$ are each ethyl or propyl, or one is propyl and the other is either methyl, phenethyl, 2-thienylethyl, or hydroxyethyl.

This invention also includes pharmaceutically acceptable salts of the compounds of Formula I formed with non-toxic organic acids. Such salts are easily prepared by methods known to the art. The base is reacted with either the calculated amount of organic or inorganic acid in a aqueous miscible solvent, such as acetone or ethanol, with isolation of the salt by concentration and cooling or an excess of the acid in aqueous immiscible solvent, such as ethyl ether, ethyl acetate or dichloromethane, with the desired salt separating directly.

Exemplary of such organic salts are those with maleic, fumaric, benzoic, ascorbic, embonic, succinic, oxalic, salicylic, methanesulfonic, ethanedisulfonic, acetic, propionic, tartaric, citric, gluconic, lactic, malic, mandelic, cinnamic, citraconic, aspartic, stearic, palmitic, itaconic, glycolic, p-amino-benzoic, glutamic, benzene sulfonic and theophylline acetic acid, as well as the 8-halotheophyllines, for example 8-bromotheophylline.

Exemplary of such inorganic salts are those with hydrochloric, hydrobromic, sulfuric, sulfamic, phosphoric and nitric acids. Of course, these salts may also be prepared by the conventional method of double decomposition of appropriate salts, which is well-known to the art.

The compounds of Formula I as well as the pharmaceutically acceptable acid addition salts thereof may be .

administered both orally and parenterally, for example in the form of tablets, capsules, powders, syrups or solutions for injection.

The invention moreover relates to a method for the preparation of the novel aminomethyl derivatives of indanes, dihydrobenzofuranes, dihydrobenzothiophenes and indolins of Formula I, which comprises:

(a) reacting a compound of the formula:

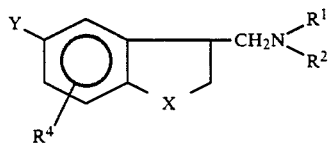

wherein Y is a hydroxy group substituted with a readily removable group selected from methyl or benzyl with a cleaving agent. X, $R^1$, $R^2$ and $R^4$ are as previously defined, or (b) hydrogenating a compound of the following formula:

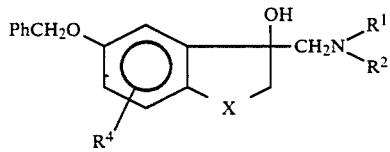

wherein X, $R^1$, $R^2$ and $R^4$ are as previously defined, or (c) reducing a compound of the following formula:

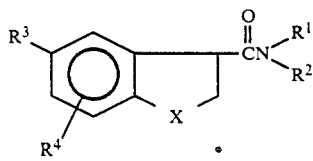

wherein X, $R^1$, $R^2$, $R^3$ and $R^4$ are as previously defined, or (d) reducing the double bond in a compound of the following formula

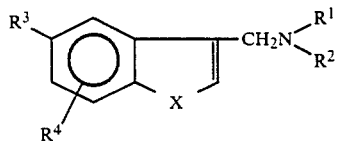

wherein X, $R^1$, $R^2$, $R^3$ and $R^4$ are as previously defined, or (e) alkylating an amine of the following formula

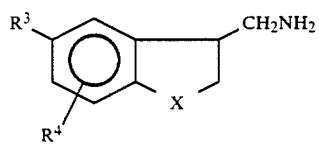

using an alkylating agent as e.g. an alkylhalide $R^1$—Y, mesylate $R^1$—OMs, tosylate $R^1$—OTs, dialkylsulphate $(R^1)_2SO_4$, an aldehyde RCHO in the presence of a reducing agent or an acylating agent RCO—Y followed by reduction of the intermediate amide. X, $R^3$ and $R^4$ are as previously defined, or (f) alkylating an amine $R^1R^2NH$ with an alkylating compound of the formula

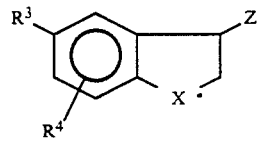

wherein Z is $CH_2$—Y, with Y being e.g. halogen, OMs and OTs, or Z is CHO in the presence of a reducing agent. X, $R^1$, $R^2$, $R^3$ and $R^4$ are as previously defined, or (g) hydrolysis of a diazonium salt of the following formula

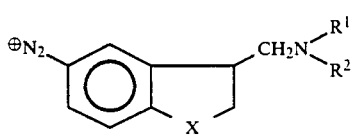

wherein X, $R^1$, $R^2$ and $R^4$ are as previously defined, and, if desired, reacting the hydroxy-group containing compound of Formula I with an acylating agent selected from $R^6$—CO—Y, $(R^6CO)_2O$, $R^6O$—CO—Y, $(R^6O-CO)_2O$, $R^7R^8N$—CO—Y, where $R^6$, $R^7$ and $R^8$ are as previously defined, and Y is halogen, whereupon the compound of Formula I obtained is isolated as the free base, or a pharmaceutically acceptable acid additions salt thereof.

The cleaving agent in method (a) is preferably a hydrogen halide acid such as hydrobromic acid or hydrogen bromide in acetic acid. Other cleaving agents such as boron tribromide, methionine in methanesulphonic acid or pyridin hydrochloride may as well be used.

When using a hydrogen halide acid as a cleaving agent the reaction is preferably carried out at reflux temperature, whereas the reaction temperature, when using boron tribromide or methionine in methanesulphonic acid as cleaving agents, preferably is kept at room temperature or below. Pyridin hydrochloride is used as a cleaving agent at temperatures in the range of 160°-200° C.

When using a hydrogen halide acid as a cleaving agent the reaction is preferably carried out in the acid itself, possibly in mixture with acetic acid; and when using boron tribromide as a cleaving agent the vehicle is preferably an inert organic solvent such as dichloromethane. Pyridin hydrochloride is used as a cleaving agent in a molar excess of 5-10 in a melt.

The optional acylation may according to the invention preferably be carried out using the appropriate acid chloride in trifluoroacetic acid, or in an inert solvent such as dichloromethane in the presence of an acid scavenger as e.g. triethylamine, or the appropriate carbamoyl chloride in DMF in the presence of a base such as potassium tert.-butoxide. Carbamates may be prepared according to classical methods from the appropriate isocyanates and hydroxy-group containing compounds of formula I in an inert organic solvent such as dichloroethane or toluene.

The hydrogenation according to method (b) may preferably be carried out in an inert organic solvent such as methanol, ethanol or ethyl acetate in the presence of a catalyst such as Raney nickel, platinum, palladium on carbon black, or the like, at or about room temperature.

The reduction according to method (c) may preferably be carried out in an inert organic solvent such as diethyl ether or tetrahydrofuran in the presence of lithium aluminium-hydride at reflux temperature.

Reduction of the double bond according to method (d) is conveniently performed with catalytic hydrogenation in an alcohol with platinum, or by hydroboration with diborane or a diborane precursor as a trimethylamine or dimethylsulphide complex in tetrahydrofuran from 0° C. to reflux temperature. The intermediate generated borane complex is hydrolysed by refluxing with dil. hydrochloric acid.

Alkylation of amines according to methods (e) and (f) is generally performed above room temperature in a suitably chosen solvent such as dichloromethane, acetone, methyl iso-butyl ketone, toluene or N-methylpyrrolidone. It may be advantageous to add a base to neutralize acidic products. When an aldehyde is used as the alkylating agent NaCNBH$_3$ is conveniently used as the reducing component.

The hydrolysis according to method (g) may preferably be carried out in aqueous sulphuric acid at elevated temperature (100–120 degrees centigrade).

The preparation of hydroxyindane derivatives (R$^3$=OH) is outlined in the following reaction scheme I:

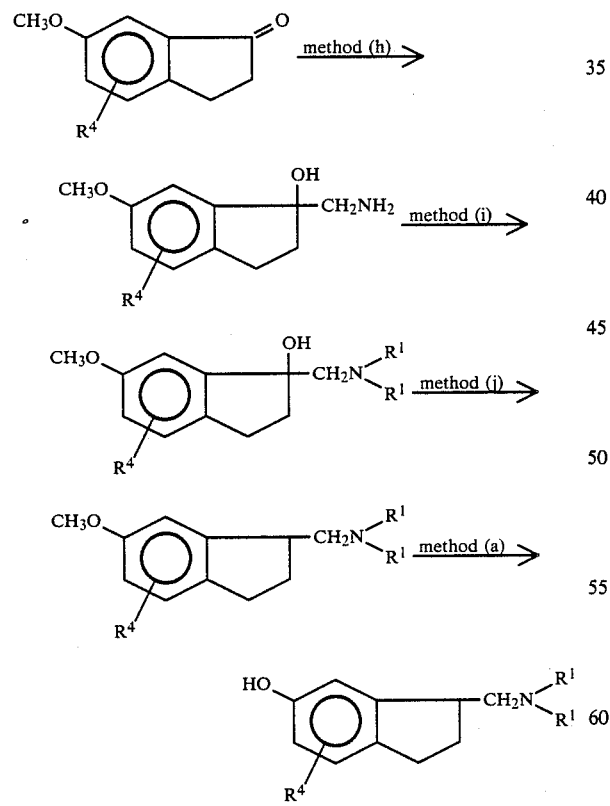

When indane derivatives are desired, wherein R$^1$ and R$^2$ are different, the preparation of such compounds is conveniently made according to the following scheme II:

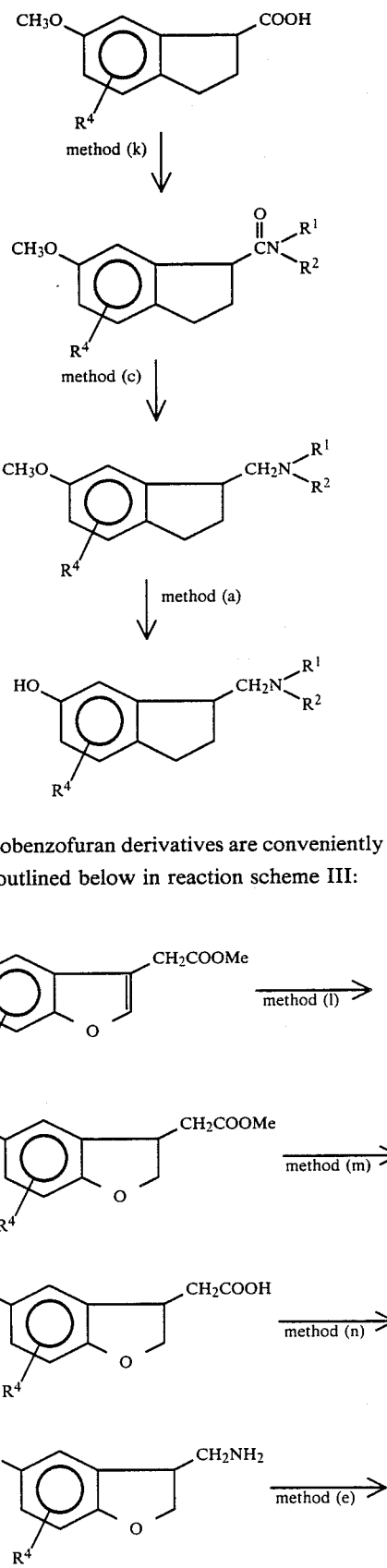

Dihydrobenzofuran derivatives are conveniently prepared as outlined below in reaction scheme III:

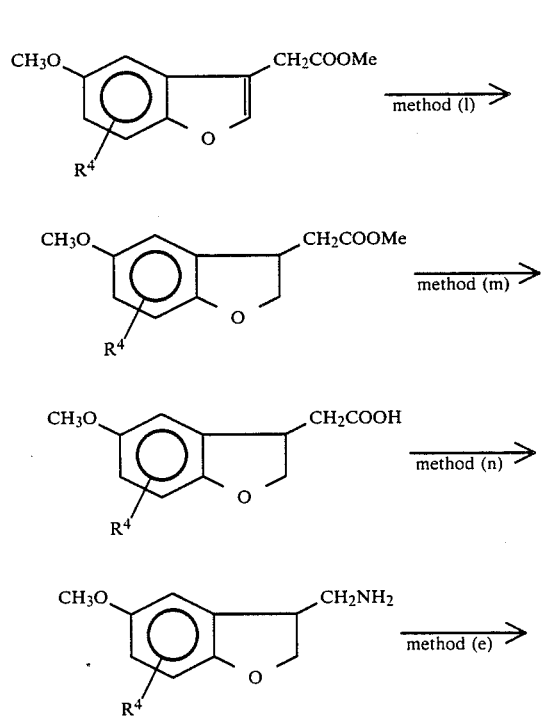

-continued

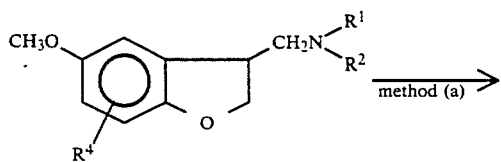

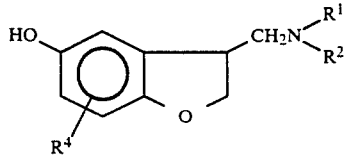

5-Nitrobenzofuran-3-carboxylic acid or 5-nitrobenzothiophene-3-carboxylic acid might also be convenient starting materials for the preparation of the corresponding dihydrobenzofurans or dihydrobenzothiophenes as outlined below in reaction scheme IV

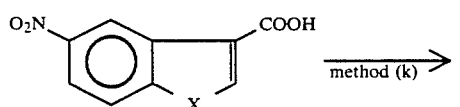

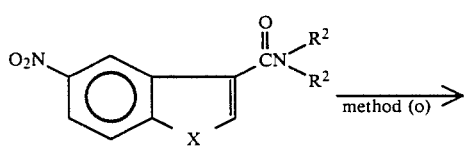

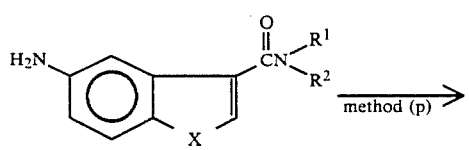

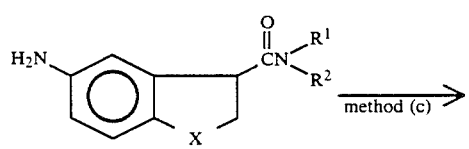

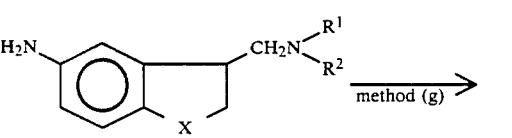

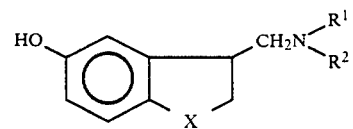

X = O or S

The intermediates of formulas II, III, IV, V, VI, VII and VIII are novel compounds and fall within the scope of the present invention.

The method of the invention will in the following be illustrated by some examples which, however, may not be construed as limiting:

EXAMPLE 1

Method (h)

1-Hydroxy-6-methoxy-1-indanmethylamine

The starting material, 6-methoxy-1-indanone, was prepared as described for 7-methoxy-1-indanone (J. D. Loudon, R. K. Razdan, J. Chem. Soc. 4 (1954) 4299).

60 g of trimethylsilyl cyanide are added via syringe to a mixture of 75 g of 6-methoxy-1-indanon, 0.8 g of anhydrous zinc iodide and 150 milliliters of anhydrous toluene. The reaction mixture was heated to 60 degrees Centigrade for 6 hours and then stirred for 16 hours without heating. To a cooled suspension of 44 g of lithium aluminium hydride in 1300 milliliters of anhydrous ether was added the solution of the unpurified cyanohydrin in ether at 0°–5° C. After the addition had been completed the reaction mixture was refluxed with stirring for 2½ hours. After cooling destruction of the excess lithium aluminium hydride was completed by cautious dropwise addition of 45 milliliters of water followed by dropwise addition of 45 milliliters of 14% sodiumhydroxide solution and subsequent addition of 190 milliliters of water. Stirring was continued for 30 minutes. Filtration and extraction with dichloromethane gave a clear organic solution which was dried over anhydrous magnesium sulphate and evaporated, and the residue was crystallized from ether. Yield: 58 grams of product.

$^1$H NMR (CDCl$_3$): 7.0 ppm(d,1H); 6.8 ppm(s, 1H); 6.7 ppm(d, 1H); 3.8 ppm(s, 3H); 2.8 ppm(s and m, 4H); 2.0–2.3 ppm(m, 6H).

EXAMPLE 2

Method (i)

N,N-dipropyl-1-hydroxy-6-methoxy-1-indanmethylamine 8.8 g of sodiumcyanoborohydride were added slowly to a mixture of 10.8 g 1-hydroxy-6-methoxy-1-indanmethylamine, 11 g of molecular sieve (3Å) and 7.9 g of propionaldehyde in 350 milliliters of methanol at a temperature of 15°–20° C. Stirring was continued at room temperature for 4 hours after the addition was completed. Additional 7.9 g of propionaldehyde and 8.8 g of sodium cyanoborohydride were added at 15°–20° C., and stirring was continued at room temperature for additional 20 hours. The reaction mixture was filtered and evaporated. The residue was dissolved in ether and the ether solution was extracted with dilute hydrochloric acid. Dichloromethane and 25% ammonium hydroxide were added until pH 10. The organic phase was washed with water, dried over anhydrous magnesium sulfate and charcoal and evaporated. The residue consisted of crude product and weighed 12 grams.

$^1$H NMR(CDCl$_3$): 6.7–7.1 ppm(m, 3H); 3.8 ppm(s, 3H); 2.1–3 ppm(m, 10H); 1.6 ppm(d. septet, 4H); 0.9 ppm(t, 6H).

EXAMPLE 3

Method (j)

N,N-dipropyl-6-methoxy-1-indanmethylamine (Lu 21-097)

12 g of N,N-dipropyl-1-hydroxy-6-methoxy-1-indanmethylamine were dissolved in 100 milliliters of methanol and 7 milliliters of concentrated hydrochloric acid and reduced catalytically with hydrogen at 3 atmospheres and 50 degrees Centigrade for 20 hours with 10 g of 5% palladium on carbon black containing 50% of water as a catalyst. After filtration of the catalyst and evaporation of the methanol 13 grams of product were obtained. The oxalate was precipitated from acetone. M.P. 124°–130° C.

EXAMPLE 4

Method (a)

N,N-dipropyl-6-hydroxy-1-indanmethylamine (Lu 21-051) 11 g of the crude N,N-dipropyl-6-methoxy-1-indanmethylamine and 130 milliliters of 48% hydrobromic acid were refluxed for 4½ hours. The reaction mixture was filtered, diluted with 300 milliliters of water, made alkaline with ammonium hydroxide solution, and extracted with ether. The ether phase was washed with water, dried, and stirred and filtered through silica gel and evaporated to give 8 grams of crude product. The oxalate salt was precipitated in acetone. M.P. 172°–181° C.

In a similar manner were prepared:

N,N-diethyl-6-hydroxy-1-indanmethylamine, oxalate. M.P. 146°–149° C. (Lu 21-096)

N,N-dimethyl-6-hydroxy-1-indanmethylamine, oxalate. M.P. 104°–107° C. (Lu 21-112). The methylation procedure (method i) was the Eschweiler-Clark procedure with formaldehyde in 98% formic acid at gentle reflux temperature.

N,N-Dibutyl-6-hydroxy-1-indanmethylamine, oxalate. M.P. 118°–121° C. (Lu 22-028)

N,N-Dipropyl-1-indanmethylamine, oxalate. M.P. 99°–102° C. (Lu 21-091)

EXAMPLE 5

(−) and (+) N,N-diethyl-6-hydroxy-1-indanmethylamine, HCl. (Lu 22-105) and (Lu 22-106)

11.2 g of N,N-diethyl-6-hydroxy-1-indanmethylamine and 19.3 g of (+)-O,O'-dibenzoyl tartaric acid were dissolved in 150 milliliters of methanol. The one enantiomer precipitated upon standing overnight at 5°–10° C. Recrystallization from 120 milliliters of methanol afforded 13.6 g of the dibenzoyltartaric acid salt of crude (−)-enantiomer. The mother liqueur contained the (+)-enantiomer. The salt was dissolved in water and, 28% sodium hydroxide was added until pH 10. Dichloromethane was added and the organic phase was separated, washed with water, dried (MgSO₄) and finally the solvent was evaporated yielding 5.2 g of product. The hydrochloric salt was precipitated by addition of HCl to a solution of the base in acetone. M.P. 174°–176° C. [α]$_D$=−24.0° (c=1, CH₃OH).

The mother liqueur containing the (+)-enantiomer was evaporated and the residue was dissolved in water. 28% sodium hydroxide were added until alkaline. Dichloromethane was added, and the organic phase was separated, washed with water, dried (MgSO₄) and the solvent evaporated. The crude base was dissolved in ether and the hydrochloric salt was subsequently precipitated by addition of HCl. Yield: 4.5 g. M.P.: 172°–175° C. [α]$_D$=+23.03° (c=1, CH₃OH).

In a similar manner, except (−)-1,1'-binaphthyl-2,2'-diylhydrogenphosphate was used instead of (+)-O,O'-dibenzoyltartaric acid, the following were prepared:

(−)-N,N-dipropyl-6-hydroxy-1-indanmethylamine. M.P. 71°–73° C., [α]$_D$=−60.9° (c=1, CH₃OH). (Lu 22-050)

(+)-N,N-dipropyl-6-hydroxy-1-indanmethylamine. M.P. 70°–73° C., [α]$_D$=+62.8° (c=1, CH₃OH). (Lu 22-049).

EXAMPLE 6

6-Benzoyloxy-N,N-dipropyl-1-indanmethylamine, oxalate (Lu 21-151)

5 g of 6-hydroxy-N,N-dipropyl-1-indanmethylamine, 25 ml of trifluoroacetic acid and 2.8 g of benzoylchloride were stirred for 2 hours at room temperature. The reaction mixture was evaporated and the residue dissolved in dichloromethane. A 10% sodium hydrogencarbonate solution was added until pH 8–9. The organic phase was separated and washed with water, dried (MgSO₄ and charcoal). Evaporation of the solvent yielded 5 g of crude base. The oxalate salt was precipitated in acetone. M.P.: 150°–163° C.

In a similar manner were prepared:

6-pivaloyloxy-N,N-diethyl-1-indanmethylamine, oxalate. M.P. 148°–152° C. (Lu 23-020)

6-(2-methylbenzoyloxy)-N,N-dipropyl-1-indanmethylamine, oxalate. M.P. 161°–167° C. (Lu 24-028)

6-(2,6-Difluorbenzoyloxy)-N,N-dipropyl-1-indanmethylamine oil. ¹H-NMR(CDCl₃): 6.9–7.5 ppm(m, 6H); 3.2 ppm(m, 1H); 2.9 ppm(t, 2H); 2.0–2.6 ppm(m, 8H); 1.2–1.6 ppm(m, 4H); 0.9 ppm(t, 6H). (Lu 24-029)

6-(2-methoxybenzoyloxy)-N,N-dipropyl-1-indanmethylamine oil. ¹H-NMR(CDCl₃): 8.0 ppm(dd, 1H); 6.9–7.6 ppm(m, 6H); 3.9 ppm(s, 3H); 3.2 ppm(m, 1H); 2.9 ppm(t, 2H); 2.0–2.6 ppm(m, 8H); 1.2–1.6 ppm(m, 4H); 0.9 ppm(t, 3H). (Lu 24-030)

6-(2-chlorobenzoyloxy)-N,N-dipropyl-1-indanmethylamine oil. ¹H-NMR(CDCl₃): 8.0 ppm(m, 1H); 7.0–7.5 ppm(m, 6H); 3.2 ppm(m, 1H); 2.9 ppm(t, 2H); 2.0–2.6 ppm(m, 8H); 1.2–1.6 ppm(m, 4H); 0.9 ppm(t, 6H). (Lu 24-031)

6-(2-acetyloxybenzoyloxy)-N,N-dipropyl-1-indanmethylamine, oxalate M.P. 144°–148° C. (Lu 24-032)

6-(2-fluorbenzoyloxy)-N,N-dipropyl-1-indanmethylamine, oxalate M.P. 159°–163° C. (Lu 24-033)

6-(N,N-dimethylaminocarbonyloxy)-N,N-dipropyl-1-indanmethylamine, oxalate M.P. 149°–150° C. (Lu 26-005)

EXAMPLE 7

6-Propylaminocarbonyloxy-N,N-diethyl-1-indanmethylamine (Lu 25-180)

2 g of 6-hydroxy-N,N-diethyl-1-indan-methylamine and 1.5 g of propylisocyanate were refluxed in 25 ml of dry toluene for 16 hours. The reaction mixture was poured into 100 ml of 0.1M acetic acid, and the organic phase was separated. The water phase was made alkaline with dil. NH₄OH and extracted with 2×50 ml diethyl ether. The combined organic phases were dried (MgSO₄) and the solvent evaporated. The residue was purified by column chromatography yielding 1.1 g of the title compound as an oil.

¹NMR(CDCl₃): 6.8–7.3 ppm (m, 3H); 5.0 ppm (broad s, 1H); 3.2 ppm (m, 3H); 1.5–3.0 ppm (m, 16H); 1.0 ppm (t, 6H); 0.9 ppm (t, 3H).

In a similar manner were prepared:

6-(3,4-dimethoxyphenylaminocarbonyloxy)-N,N-dipropylamino-1-indanmethylamine M.P. 96°–98° C. (Lu 25-169)

6-(4-isopropylphenylaminocarbonyloxy)-N,N-diethyl-1-indamethylamine, oxalate M.P. 98°-101° C. (Lu 25-177).

EXAMPLE 8

Method (k)

6-Methoxy-N-propyl-N-(2-phenylethyl)-1-indanamide

The starting material, 6-methoxyindane-1-carboxylic acid, was prepared according to V. Asham and W. H. Linnell (J. Chem. Soc. (1954) 4691).

2.5 g of 6-methoxyindane-1-carboxylic acid were mixed with 5 ml of thionylchloride and two drops of DMF. The mixture was kept at about 50° C. for two hours while stirring and then evaporated. To remove the last traces of thionylchloride the reaction mixture was evaporated with 50 ml of hexane. The residue consisted of crude 6-methoxyindane-1-carboxylic acid chloride and weighed 2.7 g. 2.7 g of the residue were added while stirring and cooling to a mixture of 4.5 ml of 9% sodium hydroxide solution and 4 g of N-propyl-2-phenylethylamine. The mixture was stirred at room temperature for 17 hours. The mixture was extracted with dichloromethane, the organic phase was separated and subsequently washed with dil.hydrochloric acid and water, dried (MgSO$_4$ and charcoal) and finally evaporated. The residual oil (5 g) was not further purified before use.

$^1$H NMR(CDCl$_3$): 7.25 ppm(s, 5H); 6.5–7.2 ppm(m, 3H); 4.2 ppm(t, 1H); 3.8 (d.s, 3H); 2–4 ppm(m, 10H); 1.6 ppm(m, 2H); 0.95 ppm(t, 3H).

EXAMPLE 9

Method (c)

6-Methoxy-N-propyl-N-(2-phenylethyl)-1-indanmethylamine

To a suspension of 1 g of lithium aluminium hydride in 15 milliliters of anhydrous ether was added a solution of 5 g of the residue of 6-methoxy-N-propyl-N-(2-phenylethyl)-1-indanamide in 15 milliliters of anhydrous ether at a rate which maintained gentle reflux of the reaction mixture. Reflux and stirring were continued for 5 hours. The reaction mixture was then stirred overnight without heating. Destruction of the excess lithium aluminium hydride was completed by cautious dropwise addition of 1 milliliter of water followed by dropwise addition of 1 milliliter of 14% sodium hydroxide solution and subsequent addition of 5 milliliters of water. Stirring was continued for 30 minutes. Filtration yielded a clear ether solution which was dried (MgSO$_4$) and evaporated, yielding 4 grams of an oil, which was used directly in the next step without further purification.

$^1$H NMR(CDCl$_3$): 7.2 ppm(s, 5H); 7.2–6.6 ppm(m, 3H); 3.8 ppm(s, 3H); 3.3 ppm(t, 1H); 2–2.8 ppm(m, 12H); 1.6 ppm(m, 2H); 0.95 ppm(t, 3H).

EXAMPLE 10

Method (a)

6-Hydroxy-N-propyl-N-(2-phenylethyl)-1-indanmethylamine (Lu 21-113)

4 g of crude 6-methoxy-N-propyl-N-(2-phenylethyl)-1-indanmethylamine, 25 milliliters of 48% aqueous hydrobromic acid, and 25 milliliters of 33% hydrogen bromide in acetic acid were refluxed for 3½ hours. After cooling the reaction mixture was partly evaporated. The residue was poured into water and made alkaline with ammonium hydroxide, and extracted with dichloromethane. The organic layers were washed with water, dried (MgSO$_4$ and charcoal) and evaporated. The residue was purified on HPLC yielding 2.7 grams of product as an oil.

$^1$H NMR(CDCl$_3$): 6.6–7.3 ppm(m, 8H); 5.5 ppm(broad s, 1H); 3.2 ppm(m, 1H); 2.0–3.0 ppm(m, 10H); 1.1–2.0 ppm(m, 4H); 0.9 ppm(t, 3H).

In a similar way were prepared:
6-Hydroxy-N-propyl-1-indanmethylamine, oxalate M.P. 210° C. (Lu 21-138)
6-Hydroxy-N-methyl-N-propyl-1-indanmethylamine M.P. 161°-165° C. (Lu 25-009).

EXAMPLE 11

Method (l)

5-Methoxy-2,3-dihydro-3-benzofuranacetic acid methylester

5-Methoxy-3-benzofuranacetic acid methylester was prepared according to the method of J. H.-T. Chan et al., Aust. J. Chem. 28. 1097–1111 (1975).

50 g of 5-methoxy-3-benzofuranacetic acid methylester were dissolved in 200 ml of ethanol, and 18 g of 5% Pd on carbon black (50% water) were added. Hydrogenation was performed at 3 ato. for 4 hours at 65° C. The catalyst was filtered off, and ethanol evaporated yielding 42 g of an oil, which was not further purified before use in the next step.

$^1$H NMR(CDCl$_3$): 6.7 ppm(m, 3H); 4.0–4.8 ppm(m, 2H); 3.8 ppm(m, 1H); 3.75 ppm(s, 3H); 3.7 ppm(s, 3H); 2.4–2.9 ppm(m, 2H).

EXAMPLE 12

Method (m)

5-Methoxy-2,3-dihydro-3-benzofuranacetic acid 110 g of 5-methoxy-2,3-dihydro-3-benzofuranacetic acid methylester dissolved in 400 ml of ethanol were added during 20 minutes to a solution of 55 g of KOH in 70 ml of water and 500 ml of ethanol at reflux temperature. Reflux was continued for 0.5 hours. Ethanol was evaporated and 600 ml of water were added, and the mixture was acidified with cold conc. hydrochloric acid and subsequently extracted with dichloromethane (3×300 ml). The combined organic phases were washed with brine, dried (MgSO$_4$) and evaporated to a volume of 200 ml. 700 ml of n-heptane were added, and excess dichloromethane evaporated. The mixture was cooled to 0° C., and the precipitated carboxylic acid filtered off. Yield: 91 g. M.P. 111°-112° C.

EXAMPLE 13

Method (f)

5-Methoxy-2,3-dihydro-3-benzofuranmethylamine

To 81 g of 5-methoxy-2,3-dihydro-3-benzofuranacetic acid in 250 ml of dichloromethane were added 0.5 ml of DMF and 48 ml of thionyl chloride. The mixture was stirred for 10 minutes and then heated at reflux for 1 hour. Dichloromethane and thionyl chloride were evaporated, and remaining traces of thionyl chloride were removed by evaporation with n-heptane. The resulting acid chloride was dissolved in 240 ml of acetone and added dropwise to a stirred solution of 25.5 g of NaN$_3$ in 120 ml of water at 10°-15° C. Cold toluene (1500 ml) was added, and the organic phase was separated, washed with brine, dried (MgSO$_4$) and finally placed in a 5 l beaker and heated slowly to 80° C. When the N₂ evolution had ceased 600 ml of conc. hydrochloric acid and 900 ml of water were added. The resulting mixture was stirred overnight at room temperature. The water phase was separated and made alkaline (pH 10–11) by addition of ammonium hydroxide and finally extracted with dichloromethane. The organic phase was evaporated and the remaining oil was dissolved in 1000 ml of dil. hydrochloric acid. This solution was left for 16 hours and then added to 600 ml of ammonium hydroxide at 0° C. Dichloromethane was added, the organic phase was separated, dried (Na₂SO₄) and evaporated yielding 61 g of product as an oil.

¹H NMR(CDCl₃): 6.7–6.8 ppm(m, 3H); 4.2–4.8 ppm(m, 2H); 3.8 ppm(s, 3H); 3.3–3.6 ppm(m, 1H); 2.9–3.0 ppm(m, 2H); 1.2 ppm(broad s, 2H).

EXAMPLE 14

Method (e)

5-Methoxy-2,3-dihydro-N,N-dipropyl-3-benzofuranmethylamine

To a solution of 22.6 g of 5-methoxy-2,3-dihydro-3-benzofuranmethylamine in 250 ml of methanol were added 23 g of mol. sieve (3 A), 25 g of propionaldehyde and during 15 minutes 27 g of NaCNBH₃ at 25°–30° C. After stirring for 4 hours 25 g of propionaldehyde and 27 g of NaCNBH₃ were added additionally. The mixture was stirred at room temperature overnight, filtered and concentrated in vacuo. The remaining mixture was dissolved in dichloromethane and water, the organic phase was separated, washed with water, dried (MgSO₄) and evaporated yielding 29.8 g of an oil. The oxalate salt was precipitated in acetone. M.P. 138°–139° C.

EXAMPLE 15

Method (a)

5-Hydroxy-2,3-dihydro-N,N-dipropyl-3-benzofuranmethylamine, hemioxalate (Lu 23-130)

11 g of 5-methoxy-2,3-dihydro-N,N-dipropyl-3-benzofuranmethylamine were mixed with 22 g of pyridin hydrochloride and heated under N₂ at about 195° C. for 1.5 hours. After cooling water and dichloromethane were added, and the mixture was made alkaline by addition of ammonium hydroxide. The organic phase was separated, dried (MgSO₄) and evaporated yielding 9 g of an oil. This oil was further purified on HPLC and finally precipitated as the hemioxalate salt in acetone. Yield: 6.8 g. M.P. 188°–191° C.

In a similar manner was prepared:
5-Hydroxy-2,3-dihydro-N,N-diethyl-3-benzofuranmethylamine, fumarate M.P. 146°–148° C. (Lu 24-088).

EXAMPLE 16

(−) and (+)-5-hydroxy-2,3-dihydro-N,N-dipropyl-3-benzofuranmethylamine, hemioxalate (Lu 24–121 and Lu 24–122)

To a solution of 21 g of 5-hydroxy-2,3-dihydro-N,N-dipropyl-3-benzofuranmethylamine in 250 ml of methanol at reflux were added 29 g of (+)-1,1′-binaphthyl-2,2′dihylhydrogenphosphate. Refluxing was continued for 20 minutes. The mixture was cooled to 0° C., and the precipitated salt was filtered off. Yield: 31 g (Frak.I). The remaining solution was evaporated and dissolved in ethyl acetate and dil. ammonium hydroxide. The ethyl acetate phase was worked up yielding 8 g of an oil. Repeated precipitation of this oil with the (−)-binaphthyl reagent yielded 10.8 g of salt, which was worked up as free base as an oil. Excess (+)-isomer crystallized from n-heptane and the remaining (−)-isomer as an oil was dissolved in acetone, and by addition of oxalic acid (−)-5-hydroxy-2,3-dihydro-N,N-dipropyl-3-benzofuranmethylamine, hemioxalate precipitated. Yield: 2.1 g. M.P. 166°–168° C. $[\alpha]_D = -17.24°$ (c=1, 0.1M methanesulphonic acid). Lu 24–121.

Frakt.I (31 g) isolated above was recrystallized from methanol twice affording 9 g of salt, which was converted to the free base as an oil. This oil was dissolved in 20 ml of n-heptane and the solution was left for 3 hours in the refrigerator. The crystalline product was filtered off and heptane evaporated leaving 1.6 g of an oil. The oil was dissolved in acetone, and by addition of oxalic acid (+)-5-hydroxy-2,3-dihydro-N,N-dipropyl-3-benzofuranmethylamine, hemioxalate precipitated. Yield: 1.2 g. M.P. 166°–168° C. $[\alpha]_D = +18.28°$ (c=1, 0.1M methanesulphonic acid). Lu 24–122.

In a similar manner were prepared:
(+) and (−)-5-hydroxy-2,3-dihydro-N-methyl-N-propyl-3-benzofuranmethylamine, oxalate. M.P. 170°–171° C. (Lu 25–020) and (Lu 25–021).

EXAMPLE 17

Method (e)

5-Methoxy-2,3-dihydro-N-methyl-N-propyl-3-benzofuranmethylamine

To 40 g of 5-methoxy-2,3-dihydro-3-benzofuranmethylamine in 400 ml of dichloromethane were added 50 ml of triethylamine. The mixture was cooled, and 35 g of propionyl chloride in 50 ml of dichloromethane were added dropwise at a rate such as to keep the temperature below 25° C. The mixture was stirred for further 16 hours at room temperature, washed with water and the organic phase separated, dried (MgSO₄) and the solvent evaporated leaving a semi-crystalline product, which crystallized from n-heptane. Yield: 48 g of 5-methoxy-2,3-dihydro-N-propionyl-3-benzofuranmethylamine. M.P. 65°–67° C.

Reduction of this amide with lithium aluminium hydride in ether was performed as in Example 9. Yield: 42 g of 5-methoxy-2,3-dihydro-N-propyl-3-benzofuranmethylamine as an oil.

¹H NMR(CDCl₃): 6.7–6.8 ppm(m, 3H); 4.2–4.8 ppm(m, 2H); 3.8 ppm(s, 3H), 3.4–3.6 ppm(m, 1H); 2.5–2.9 ppm(m, 4H); 1.2–1.6 ppm(m, 3H); 0.9 ppm(t, 3H).

To an ice cooled solution of 11 g of 5-methoxy-2,3-dihydro-N-propyl-3-benzofuranmethylamine in 30 ml of formic acid were added 13 ml of a 37% formaldehyde solution. The mixture was gently refluxed for 3 hours and subsequently poured onto ice. Dichloromethane and conc. ammonium hydroxyde (until pH=10) were added. The organic phase was separated, washed with water, dried (MgSO₄) and finally evaporated leaving 11 g of an oil. Purification by column chromatography on silica gel yielded 8 g of 5-methoxy-2,3-dihydro-N-methyl-N-propyl-3-benzofuranmethylamine as an oil.

¹H NMR(CDCl₃): 6.7–6.8 ppm(m, 3H); 4.2–4.8 ppm(m, 2H); 3.8 ppm(s, 3H); 3.4–3.7 ppm(m, 1H); 2.2–2.6 ppm(m, 4H); 2.2 ppm(s, 3H); 1.2–1.6 ppm(m, 2H); 0.9 ppm(t, 3H).

EXAMPLE 18

Method (a)

5-Hydroxy-2,3-dihydro-N-methyl-N-propyl-3-benzofuranmethylamine, oxalate (Lu 24–103)

Cleavage of the 5-methoxy group of 5-methoxy-2,3-dihydro-N-methyl-N-propyl-3-benzofuranmethylamine was performed with pyridin hydrogenchloride as in Example 18. The resulting oil was purified on HPLC yielding 4 g of the title compound from 8 g of the 5-methoxy derivative. The oxalate salt was precipitated in acetone. M.P. 138°–139° C.

In a similar manner were prepared:

5-Hydroxy-2,3-dihydro-N-(2-hydroxyethyl)-N-propyl-3-benzofuranmethylamine, oxalate M.P. 118°–120° C. (Lu 24–102)

5-Hydroxy-2,3-dihydro-N-(2-phenylethyl)-N-propyl-3-benzofuranmethylamine Oil $^1$H NMR(CDCl$_3$): 7.2 ppm(m, 5H); 6.6 ppm(m, 3H); 5.1 ppm(broad s, 1H); 4.2–4.5 ppm(m, 2H); 3.3–3.6 ppm(m, 1H); 2.4–2.8 ppm(m, 8H); 1.2–1.6 ppm(m, 2H); 0.9 ppm(t, 3H). (Lu 24–084).

5-Hydroxy-2,3-dihydro-N-propyl-N-(2-thienyl-2-ethyl)-3-benzofuranmethylamine Oil $^1$H NMR(CDCl$_3$): 6.5–7.2 ppm(m, 6H); 4.2–4.6 ppm(m, 2H); 3.4–3.6 ppm(m, 1H); 2.4–3.0 ppm(m, 8H); 1.2–1.6 ppm(m, 2H); 0.9 ppm(t, 3H). (Lu 24–155).

The following acylated derivates of 2,3-dihydrobenzofuranes were prepared in a similar manner as in Examples 6 and 7:

5-Pivaloyloxy-2,3-dihydro-N,N-dipropyl-3-benzofuranmethylamine, oxalate M.P. 160°–164° C. (Lu 24–042)

5-(2-Methylbenzoyloxy)-2,3-dihydro-N,N-dipropyl-3-benzofuranmethylamine, oxalate M.P. 162°–165° C. (Lu 24–074)

5-(2-aminobenzoyloxy)-2,3-dihydro-N,N-dipropyl-3-benzofuranmethylamine, oxalate M.P. 110°–115° C. (Lu 25–165)

5-Pivaloyloxymethyloxy-2,3-dihydro-N,N-dipropyl-3-benzofuranmethylamine Oil $^1$H NMR(CDCl$_3$): 6.6–6.9 ppm(m, 3H); 5.6 ppm(s, 2H); 4.2–4.6 ppm(m, 2H); 3.4–3.6 ppm(m, 1H); 2.2–2.6 ppm(m, 6H); 1.2–1.6 ppm(m, 4H); 1.2 ppm(s, 9H); 0.9 ppm(t, 6H). (Lu 24–104)

5-isopropylaminocarbonyloxy-2,3-dihydro-N,N-dipropyl-3-benzofuranmethylamine, oxalate M.P. 135°–137° C. (Lu 25–158)

5-(3,4-dimethoxyphenylaminocarboxyloxy)-2,3-dihydro-N,N-dipropyl-3-benzofuranmethylamine, oxalate. M.P. 96°–97° C. (Lu 25–168)

5-(n-nonylaminocarbonyloxy)-2,3-dihydro-N,N-dipropyl-3-benzofuranmethylamine, oxalate. M.P. 80°–100° C. (Lu 25–170)

5-(4-tolylaminocarbonyloxy)-2,3-dihydro-N,N-dipropyl-3-benzofuranmethylamine M.P. 131°–133° C. (Lu 25–171)

5-(4-isopropylphenylaminocarbonyloxy)-2,3-dihydro-N,N-dipropyl-3-benzofuranmethylamine. M.P. 104°–105° C. (Lu 25–176)

5-(4-isopropylphenylaminocarbonyloxy)-2,3-dihydro-N-methyl-N-propyl-3-benzofuranmethyl-amine. M.P. 93° C. (Lu 25–178)

5-propylaminocarbonyloxy-2,3-dihydro-N-methyl-N-propyl-3-benzofuranmethylamine M.P. 89°–91° C. (Lu 25–179)

5-propylaminocarbonyloxy-2,3-dihydro-N,N-dipropylamino-3-benzofuranmethylamine, oxalate M.P. 92°–108° C. (Lu 26–002).

EXAMPLE 19

Method (k)

5-Nitro-N,N-dipropyl-3-benzothiophencarboxamide

5-Nitro-3-benzothiophencarboxylic acid was prepared according to the methods given in F. G. Bordwell and C. G. Albisetti, J. Amer. Chem. Soc. 70, 1955 (1948) and M. Martin-Smith et al., J. Chem. Soc. (c) 1967, 1899.

45 g of 5-nitro-3-benzothiophencarboxylic acid were suspended in 150 ml of 1,1,1-trichloroethane. 100 ml of thionyl chloride and 0.5 ml of DMF were added. The mixture was refluxed for 2 hours resulting in a clear solution. The solvents were evaporated and remaining thionyl chloride was removed by evaporation twice with toluene. The crystalline product thus obtained was added in small portions to a solution of 60 g of dipropylamine in 500 ml of dichloromethane below 10° C. The mixture was heated to 30° C. and eluted through 200 g of silica gel with 1500 ml of a mixture (1:1) of dichloromethane and ethyl acetate. The organic phase was washed with water, dried (MgSO$_4$) and evaporated. 200 ml of n-heptane were added and the crystalline product filtered off. Yield: 56 g. M.P. 100° C.

EXAMPLE 20

Method (o)

5-Amino-N,N-dipropyl-3-benzothiophencarboxamide 80 g of 5-nitro-N,N-dipropyl-3-benzothiophencarboxamide were reduced with Fe-powder in 90% ethanol as in Example 11. Yield of title compound: 75 g as a semicrystalline product. $^1$H NMR(CDCl$_3$): 7.0 ppm(d, 1H); 6.5 ppm(d, 1H); 6.3 ppm(s, 1H); 4.4 ppm(dd, 1H); 3.0–3.9 ppm(m, 8H); 1.4–1.9 ppm(m, 4H); 0.9 ppm(d. t., 6H).

EXAMPLE 21

Method (p)

5-Amino-2,3-dihydro-N,N-dipropyl-3-benzothiophencarboxamide 30 g of 5-amino-N,N-dipropyl-3-benzothiophencarboxamide were dissolved in 250 ml of dry methanol. 15 g of magnesium turnings were added (eventually activated by addition of a few drops of 1,2-dibromoethane). The mixture was stirred at 30°–35° C. for 4 hours with periodically cooling to keep the temperature down. 2 l of a saturated ammonium chloride solution were added and the product extracted with ethyl acetate. The organic phase was separated, washed with water, dried (MgSO$_4$) and the solvent evaporated. Isopropyl ether was added, and by cooling the title compound precipitated and was filtered off. Yield: 20 g. M.P. 100° C.

EXAMPLE 22

Method (g)

5-Hydroxy-2,3-dihydro-N,N-dipropyl-3-benzothiophencarboxamide 11.6 g of 5-amino-2,3-dihydro-N,N-dipropyl-3-benzothiophencarboxamide were dissolved in a mixture of 4 ml of conc. sulphuric acid and 40 ml of water. 3.1 g of sodium nitrite dissolved in 10 ml of water were added dropwise below 10° C. with stirring. After addition the mixture was stirred for further 0.5 hours. The diazonium solution was then added carefully to a pre-heated solution of 50 ml of conc. sulphuric acid in 40 ml of water at 115°–120° C. The resulting mixture was poured onto ice and subsequently extracted with dichloromethane. Yield of the title compound as a semicrystalline product: 8.7 g.

$^1$H NMR(CDCl$_3$): 7.3 ppm(s, 1H); 6.9 ppm(d, 1H); 6.4–6.6 ppm(m, 2H); 4.5 ppm(dd, 1H); 3.1–3.9 ppm(m, 6H); 1.5–1.8 ppm(m, 4H); 0.9 ppm(t, 6H).

EXAMPLE 23

Method (c)

5-Hydroxy-2,3-dihydroxy-N,N-dipropyl-3-benzothiophenmethylamine, hemifumarate (Lu 24–100)

8.7 g of 5-hydroxy-2,3-dihydro-N,N-dipropyl-3-benzothiophencarboxamide were reduced with 5 g of lithium aluminium hydride in anh. tetrahydrofuran as in Example 12. The title compound was isolated as an oil and subsequently crystallized as the hemifumarate salt from acetone/ethanol (2:1). Yield: 5.9 g. M.P. 138°–140° C.

The new compounds of Formula I were tested in reliable and recognized pharmacological tests in animals. Where the compounds were administered as an acid addition salt, the doses were calculated as the free amine.

DA stimulating activities are reflected in the ability of the compounds to induce motility inhibition in rats.

Furthermore, the potency of the drug to induce contralateral circling behaviour in 6-hydroxy-DA-lesioned rats was determined. The specificity of this receptor resembles that of the presynaptic DA receptors mediating motility inhibition. Selectivity for the DA-autoreceptor is demonstrated by inability of the compounds to reverse hypomotility in reserpine and alpha-methyl-p-tyrosine pretreated rats.

PHARMACOLOGICAL METHODS

The experiments were made according to published methods, using rats of the Wistar strain.

The effect on dopamine DA-autoreceptors was studied by measuring the ability of the test compound to reduce spontaneous locomotor activity as described before (Arnt et al., 1983). However, this effect is not specific for DA-autoreceptor agonists. Therefore, also the ability of a test compound to induce contralateral circling in rats with unilateral 6-hydroxy-DA lesions was evaluated (loc cit.). This effect is specific for DA-receptor agonists but does not discriminate between autoreceptors and post-synaptic DA-receptor agonists. In order to evaluate the activity on postsynaptic DA-receptors the effect of the test compound to reverse the locomotor depression was studied in rats depleted of DA using previous treatment with reserpine plus alphamethyl-p-tyrosine (Bøgesø et al., 1987). In this model selective autoreceptor agonists like (−)-3-PPP are without effect.

References:

Arnt, J., Bøgesø, K. P., Christensen, A. V., Hyttel, J., Lassen J. J., Svendsen, O.; Psychopharmacology 1983, 81, 199–207.

Bøgesø, K. P., Arnt, J., Lundmark, M., Sundell, S.; J. Med. Chem., 1987, 30, 142–150.

| Compound Code no | Motility Inh.[1] rats (sc) ED$_{50}$ (μmol/kg) | 6-OHDA Contr.Circl.[1] rats (sc) ED$_{50}$ (μmol/kg) | Reserpin α-Mt Rev.[1] rats (sc) % at 5 μmol/kg or ED$_{50}$ (μmol/kg) |
|---|---|---|---|
| Lu 21-051 | 0.45 | 0.35 | 44% |
| Lu 21-091 | >62 | >62 | NT |
| Lu 21-096 | 1.0 | 0.19 | 50% |
| Lu 21-097 | >14 | >14 | NT |
| Lu 21-112 | 5.7 | 0.95 | 12 |
| Lu 21-113 | 0.51 | 0.12 | 63% |
| Lu 21-138 | 19 | 10 | NT |
| Lu 22-028 | 13 | >14 | NT |
| Lu 22-049 | 0.26 | 0.18 | 4.5 |
| Lu 22-050 | 1.3 | 0.45 | 60 |
| Lu 22-105 | 0.87 | 1.2 | 120 |
| Lu 22-106 | 1.1 | 0.36 | 14 |
| Lu 23-020 | 0.84 | 0.33 | NT |
| Lu 23-130 | 0.5–2 | 0.35 | 3.4 |
| Lu 24-028 | NT | Duration 18 hrs | NT |
| Lu 24-029 | NT | Duration 4 hrs | NT |
| Lu 24-030 | NT | Duration 4 hrs | NT |
| Lu 24-031 | NT | Duration 4 hrs | NT |
| Lu 24-032 | NT | Duration 4 hrs | NT |
| Lu 24-033 | NT | Duration 4 hrs | NT |
| Lu 24-042 | NT | 0.40 | NT |
| Lu 24-074 | NT | Duration 15 hrs | NT |
| Lu 24-084 | 1.9 | 0.94 | 11 |
| Lu 24-088 | 1.7 | 1.2 | 13% |
| Lu 24-100 | 3.0 | 4.6 | 20 |
| Lu 24-102 | 5.4 | 2.1 | 19 |
| Lu 24-103 | 4.5 | 1.2 | 290 |
| Lu 24-104 | NT | Activity as Lu 23-130 | NT |
| Lu 24-121 | 5.4 | 1.7 | 86 |
| Lu 24-122 | 0.81 | 0.16 | NT |
| Lu 24-155 | 7.0 | 1.2 | 28 |
| Lu 25-009 | 0.65 | 0.82 | 66 |
| Lu 25-020 | 4.1 | 0.95 | 65 |
| Lu 25-021 | 5.4 | 5.2 | 290 |
| Lu 25-158 | NT | Duration 4 hrs | NT |
| Lu 25-165 | NT | Duration >6 hrs | NT |
| Lu 25-168 | NT | NT | NT |

| Compound Code no | Motility Inh.[1] rats (sc) ED$_{50}$ (μmol/kg) | 6-OHDA Contr.Circl.[1] rats (sc) ED$_{50}$ (μmol/kg) | Reserpin α-Mt Rev.[1] rats (sc) % at 5 μmol/kg or ED$_{50}$ (μmol/kg) |
|---|---|---|---|
| Lu 25-169 | NT | NT | NT |
| Lu 25-170 | NT | NT | NT |
| Lu 25-171 | NT | NT | NT |
| Lu 25-176 | NT | NT | NT |
| Lu 25-177 | NT | Duration >6 hrs | NT |
| Lu 25-178 | NT | NT | NT |
| Lu 25-179 | NT | NT | NT |
| Lu 25-180 | NT | NT | NT |
| Lu 26-002 | NT | NT | NT |
| Lu 26-005 | NT | NT | NT |
| Apomorphine | 0.64 | 0.06 | 0.27 |
| (-)-3-PPP | 4.2-11 | 0.77 | >67 |

[1]NT: Not tested.

The compounds of Formula I and the non-toxic acid addition salts thereof may be adminstered to animals such as dogs, cats, horses, sheep or the like, including human beings, both orally and parenterally, and may be used for example in the form of tablets, capsules, powders, syrups-or in the form of the usual sterile solutions for injection.

Most conveniently, the compounds of Formula I are administered orally in unit dosage form such as tablets or capsules, each dosage unit containing a non-toxic acid addition salt of one of said compounds in an amount of from about 0.10 mg to about 100 mg, most preferably however, from about 5 mg to 50 mg, calculated as the free amine, the total daily dosage usually ranging from about 1 mg to about 500 mg. The exact individual dosages as well as daily dosages in a particular case will, of course, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums or the like.

When the compound of Formula I is an ester, preferably a decanoic acid ester, palmitic acid ester or a behenic acid ester, the composition may advantageously be an oily solution for injection, and such solutions often have a very prolonged effect when compared with the corresponding unesterified compound.

Typical examples of formulas for composition containing 2,3-dihydro-3-(N,N-dipropylaminomethyl)-5-hydroxybenzofuran (called Lu 23–130 for short) as the active ingredient, are as follows:

| (1) Tablets containing 5 milligrams of Lu 23-130 calculated as the free base: | |
|---|---|
| Lu 23-130 | 5 mg |
| Lactose | 18 mg |
| Potato starch | 27 mg |
| Saccharose | 58 mg |
| Sorbitol | 3 mg |
| Talcum | 5 mg |
| Gelatine | 2 mg |
| Povidone | 1 mg |
| Magnesium stearate | 0.5 mg |
| (2) Tablets containing 50 milligrams of Lu 23-130 calculated as the free base: | |
| Lu 23-130 | 50 mg |
| Lactose | 16 mg |
| Potato starch | 45 mg |
| Saccharose | 106 mg |
| Sorbitol | 6 mg |
| Talcum | 9 mg |
| Gelatine | 4 mg |
| Povidone | 3 mg |
| Magnesium stearate | 0.6 mg |
| (3) Syrup containing per milliliter: | |
| Lu 23-130 | 10 mg |
| Sorbitol | 500 mg |
| Tragacanth | 7 mg |
| Glycerol | 50 mg |
| Methyl-paraben | 1 mg |
| Porpyl-paraben | 0.1 mg |
| Ethanol | 0.005 ml |
| Water | ad 1 ml |
| (4) Solution for injection containing per milliliter: | |
| Lu 23-130 | 50 mg |
| Acetic acid | 17.9 mg |
| Sterile water | ad 1 ml |
| (5) Solution for injection containing per milliliter: | |
| Lu 23-130 | 10 mg |
| Sorbitol | 42.9 mg |
| Acetic acid | 0.63 mg |
| Sodium hydroxide | 22 mg |
| Sterile water | ad 1 ml |

Any other pharmaceutical tableting adjucants may be used provided that they are compatible with the active ingredient, and additional compositions and dosage forms may be similar to those presently used for neuroleptics, such as thiothixene, clopenthixol or flupenthixol.

Also combinations of the compounds of Formula I as well as their non-toxic acid salts with other active ingredients, especially other neuroleptics, thymoleptics, tranquilizers, analgetics or the like, fall within the scope of the present invention.

As previously stated, when isolating the compounds of Formula I in the form of an acid addition salt the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanes ulphonates, ethane sulphonates, lactates, citrates, tartrates or bitartrates, embonates and maleates of the amines of Formula I. Other acids are likewise suitable and may be employed if desired. For example, fumaric, benzoic, ascorbic, succinic, salicylic, bismethylene salicylic, propionic, gluconic, malic, malonic, mandelic, cannamic, citraconic, stearic, palmitic, itaconic, glycolic, benzene sulphonic, and sulphamic acids may also be employed as acid addition saltforming acids.

When it is desired to isolate a compound of the invention in the form of the free base, this may be done according to conventional procedure as by dissolving the isolated or unisolated salt in water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation or inhibition of the manifestations of certain physiological-psychological abnormalies of animals, including psychoses, depressions, pains or the like, by administering to a living animal body, including human beings, an adequate quantity of a compound of Formula I or a non-toxic acid addition salt thereof. An adequate quantity would be from about 0.001 mg to about 10 mg per kg of body weight in each unit dosage, and from about 0.05 mg to about 1000 mg as a unit dosage per day.

It is to be understood that the invention is not limited to the exact details of operation or exact compound or compositions shown and described, as obvious modifications and equivalents will be apparent to one skilled in the art.

We claim:

1. Indane compound of the following formula:

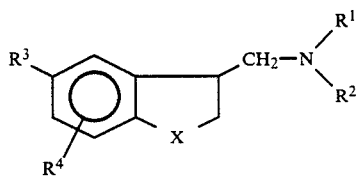

I wherein X is $CH_2$, $R^1$ is hydrogen, lower alkyl (1-6 C-atoms) or lower alkenyl (2-6 C-atoms), branched or unbranched, optionally substituted with a hydroxy group, aralkyl with from 4-13 C-atoms inclusive, the aromatic group being phenyl, thienyl, or cycloalkyl (3-6 C-atoms), $R^2$ is hydrogen, lower alkyl (1-6 C-atoms), branched or unbranched, provided that both $R^1$ and $R^2$ may not be hydrogen, $R^3$ is hydroxy, optionally substituted with

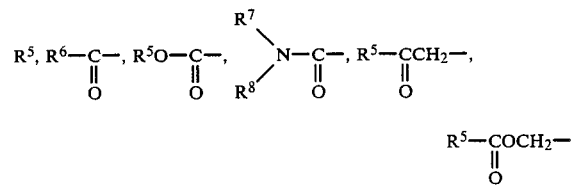

in which $R^5$ is alkyl (1-20 C-atoms), branched or unbranched, cycloalkyl (3-6 C-atoms), adamantyl, aralkyl (4-13 C-atoms inclusive) or a phenyl or lower-alkyl phenyl group, $R^6$ is hydrogen or as $R^5$, $R^7$ and $R^8$ are defined as $R^6$, $R^4$ is hydrogen, halogen, lower alkyl (1-6 C-atoms), branched or unbranched, trifluoromethyl, cyano, nitro, SH, or $NH_2$ optionally substituted as shown above for $R^3$, as well as enantiomers thereof, or a pharmaceutically-acceptable acid addition salt thereof.

2. A compound according to claim 1, wherein X is $CH_2$, $R^3$ is hydroxy or an acylated derivative thereof, $R^4$ is hydrogen, and $R^1$ and $R^2$ are each ethyl or propyl, or one is propyl and the other is either methyl, phenethyl, 2-thienylethyl or hydroxyethyl.

3. Compound of claim 1 selected from
1-(N,N-diethylaminomethyl)-6-hydroxy indane
1-(N-propyl-N-(2-phenylethyl)-aminomethyl)-6-hydroxy indane
1-(N-methyl)-N-propylaminomethyl)-6-hydroxy indane and
1-(N,N-dipropylaminomethyl)-6-hydroxy indane
and enantiomers and non-toxic acid addition salts thereof.

4. A pharmaceutical composition suitable for treating dopamine-related central nervous system disorders in unit dosage form comprising—as an active ingredient—a compound as defined in claim 1, and one or more pharmaceutical diluents or carriers.

5. A pharmaceutical composition in unit dosage form, according to claim 4, wherein the active ingredient is present in an amount from 0.1-100 milligrams per unit dosage.

6. A method for the treatment of dopamine-related disorders of the central nervous system, comprising administering an effective amount of a compound of claim 1, as an active ingredient, and one or more pharmaceutical diluents or carriers, to a warmblooded animal.

7. A method according to claim 6, wherein the active ingredient is present in an amount from 0.1 to about 100 mg per unit dosage.

8. A method for the treatment of dopamine-related disorders of the central nervous system, comprising the step of administering an effective amount of a compound of claim 1, as active ingredient, to a warmblooded animal in need thereof.

9. A method according to claim 8, wherein the active ingredient is present in an amount of about 0.1 to about 100 mg per unit dosage.

10. The method of claim 6 wherein the animal is a human being.

11. A method of claim 8 wherein the animal is a human being.

* * * * *

UNITED STATES PATENT AND TRADEMARK OFFICE
CERTIFICATE OF CORRECTION

PATENT NO. : 4,946,863

DATED : Aug. 7, 1990

INVENTOR(S) : Klaus P. Boegesoe, Jens K. Perregaard

It is certified that error appears in the above-identified patent and that said Letters Patent is hereby corrected as shown below:

Column 10, line 62; "$^1$NMR" should read -- $^1$H NMR --.

Column 20, approximate line 28; "Porpyl-paraben" should read -- Propyl-paraben --.

Column 21, line 11/12; "abnormalies" should read -- abnormalities --.

Column 21, line 27; "compound" should read -- compounds --.
(R&A 1-18-89, P. 1).

Signed and Sealed this

Twenty-fifth Day of February, 1992

Attest:

HARRY F. MANBECK, JR.

*Attesting Officer*  *Commissioner of Patents and Trademarks*